(12) United States Patent
Giltz (10) Patent No.: US 10,718,796 B1
(45) Date of Patent: Jul. 21, 2020

(54) MULTITASK MULTIFUNCTION APPARATUS FOR BUILDING INSPECTION

(71) Applicant: Richard Giltz, Sterling Heights, MI (US)

(72) Inventor: Richard Giltz, Sterling Heights, MI (US)

( * ) Notice: Subject to any disclaimer, the term of this patent is extended or adjusted under 35 U.S.C. 154(b) by 0 days.

(21) Appl. No.: 16/371,839

(22) Filed: Apr. 1, 2019

Related U.S. Application Data (60) Provisional application No. 62/619,700, filed on Jan. 30, 2018.

(51) Int. Cl.
   *G01R 19/00* (2006.01)
   *G01N 33/00* (2006.01)
   (Continued)

(52) U.S. Cl.
   CPC ............ *G01R 19/0084* (2013.01); *F21L 4/00* (2013.01); *F41B 13/00* (2013.01); *F41H 9/10* (2013.01); *G01K 1/08* (2013.01); *G01N 1/2226* (2013.01); *G01N 1/2273* (2013.01); *G01N 19/10* (2013.01); *G01N 33/004* (2013.01); *G01N 33/0031* (2013.01); *G01N 33/0036* (2013.01);
   (Continued)

(58) Field of Classification Search
   CPC ....... G01R 19/0084; G01R 19/14; F21L 4/00; F41H 9/10; G01K 1/08; F41B 13/00; G01N 33/004; G01N 19/10; G01N 33/0004; G01N 1/2273; G01N 33/0075; G01N 33/0036; G01N 1/2226; G01N 33/0031; G01N 2001/2223; G01N 2015/0046; G01T 1/178; F21Y 2115/10; F24F 2110/50; F24F 2110/70; F24F 2110/72
   See application file for complete search history.

(56) References Cited

U.S. PATENT DOCUMENTS

| 5,428,964 A | * | 7/1995 | Lobdell | G05D 27/02 62/176.6 |
| 10,324,030 B2 | * | 6/2019 | Sanroma | G01N 33/225 |

(Continued)

FOREIGN PATENT DOCUMENTS

KR     20090008930 A   *  1/2009

OTHER PUBLICATIONS

English machine translation for document KR20090008930.*

*Primary Examiner* — Daniel S Larkin
*Assistant Examiner* — Anthony W Megna Fuentes
(74) *Attorney, Agent, or Firm* — Jacob M. Ward; Ward Law Office LLC (57) ABSTRACT

A multifunction multitask apparatus for use in building inspections is disclosed. The apparatus comprises a portable case comprising a grippable handle, a mini-desk, lighting elements and a plurality of sensors for building structure inspection. The apparatus includes a power source in electric communication with a sensor. The apparatus may include a variety of sensors including a voltage tester, a circuit polarity sensor, and ambient air testing sensor, and ambient temperature sensor, and ambient humidity sensor, a moisture meter, a radon sensor, a carbon monoxide sensor, and an airborne toxin sensor. Other embodiments of the invention may include safety features including a first-aid cat, a chemical spray deterrent device, and a tactical prong. Other embodiments may include lights including a laser pointer, an LED light, an a focused light beam.

15 Claims, 6 Drawing Sheets

(51) Int. Cl.
*G01N 1/22* (2006.01)
*F21L 4/00* (2006.01)
*F41H 9/10* (2006.01)
*G01K 1/08* (2006.01)
*F41B 13/00* (2006.01)
*G01R 19/14* (2006.01)
*G01N 19/10* (2006.01)
*G01T 1/178* (2006.01)
*G01N 15/00* (2006.01)
*F21Y 115/10* (2016.01)
*F24F 110/72* (2018.01)

(52) U.S. Cl.
CPC ......... *G01N 33/0075* (2013.01); *G01R 19/14* (2013.01); *G01T 1/178* (2013.01); *F21Y 2115/10* (2016.08); *F24F 2110/72* (2018.01); *G01N 2001/2223* (2013.01); *G01N 2015/0046* (2013.01)

(56) References Cited

U.S. PATENT DOCUMENTS

| | | | | |
|---|---|---|---|---|
| 2003/0123254 A1* | 7/2003 | Brass | ................ | G01N 21/6447 |
| | | | | 362/231 |
| 2003/0218469 A1* | 11/2003 | Brazell | .................... | G01V 3/15 |
| | | | | 324/637 |
| 2014/0120977 A1* | 5/2014 | Amis | .................... | H04W 4/023 |
| | | | | 455/521 |
| 2015/0022368 A1* | 1/2015 | Smith | ....................... | G05F 1/46 |
| | | | | 340/693.3 |
| 2018/0242880 A1* | 8/2018 | Bhushan | ................ | G01R 33/07 |

* cited by examiner

MULTITASK MULTIFUNCTION APPARATUS FOR BUILDING INSPECTION

BACKGROUND

The field of the invention is multi-function tools, particularly those for use in confined building inspection applications including attics, crawlspaces, and other closed areas.

At various times during the service life of a building, the structure and related property may be subject to an inspection. Some building inspections may be performed to determine compliance with building or safety codes. Other inspections may be performed in connection with the sale or change in occupancy of a building, or portion thereof, to identify structural, code, or safety issues. Inspections may be performed by any number of skilled inspectors, including government building or code inspectors, private home inspectors, construction contractors, and even individual homeowners.

In order to adequately perform an inspection, property inspectors and other building trades professionals frequently require ready access to multiple instruments, each designed to assess one or more conditions of the building structure or surrounding areas. The property inspector must access the instruments when inspecting a structure, which may include multiple living levels, basements, attics, garages, outbuildings, and other structures. In addition, building trades professionals similarly require access to multiple instruments when evaluating compliance with applicable building and code specifications. For both applications, there is an acute need to have multiple function instruments ready at hand. The inability to readily access a functional instrument, such as a meter or sensor, together with an appropriate power source can make the task of inspecting a property or verifying compliance with applicable building specifications and codes inefficient, more difficult, and unreliable. The instruments needed are often too numerous for the inspector to carry in their hands or in clothing pockets. The need to repeatedly exit and reenter a confined space to retrieve an instrument may increase the time necessary to complete an inspection and may expose the inspector to unnecessary hazards.

Among other things, a property inspector or building trades professional may overlook a test if a sensor or instrument is not readily available. In addition, lack of ready access to an instrument or sensor may delay an inspection, waste time, and add expense.

The need for a property inspector or building trade professional to have ready access to multiple functional instruments is particularly acute when the inspection concerns a confined space, such as a cellar, basement, crawlspace, or attic. In those environments, the property inspector or building trades professional may face poor lighting, inadequate ventilation, hazardous surfaces, dangerous materials, pests and vermin, and limited ability to move about. Lack of ready access to a multiple functional instrument may expose the inspector to hazards, and may degrade the quality of measurements and other observations of the condition of the property.

In addition, confined spaces in buildings often expose inspectors to health and safety hazards, including animals (such as dogs, raccoons, and other wild or aggressive animals), insects, reptiles, sharp objects, noxious or poisonous fumes, and chemical hazards such as asbestos and other friable building materials. A need exists during such inspections for ready access to devices to mitigate the hazards and their impact.

It is recognized that a need exists for a portable, self-contained, battery-powered, multiple functional instrument apparatus containing those instruments and sensors most commonly used by property inspectors and building trades professionals. The need is particularly acute for a device containing multiple instruments and sensors used by inspectors and other professionals in confined spaces such as cellars, basements, crawlspaces, or attics. The device should be portable, lightweight, and able to be maneuvered in confined spaces. The instruments and sensors present in the device should be accurate and provide data permitting the property inspector or building trades professional to evaluate compliance with building codes, health codes, building blueprints, and other regulations or specifications. The device should be usable in extreme conditions, including extreme temperatures, darkness, dusty and dirty spaces, dampness, and other environmental extremes.

BRIEF DESCRIPTION

Figure 1:
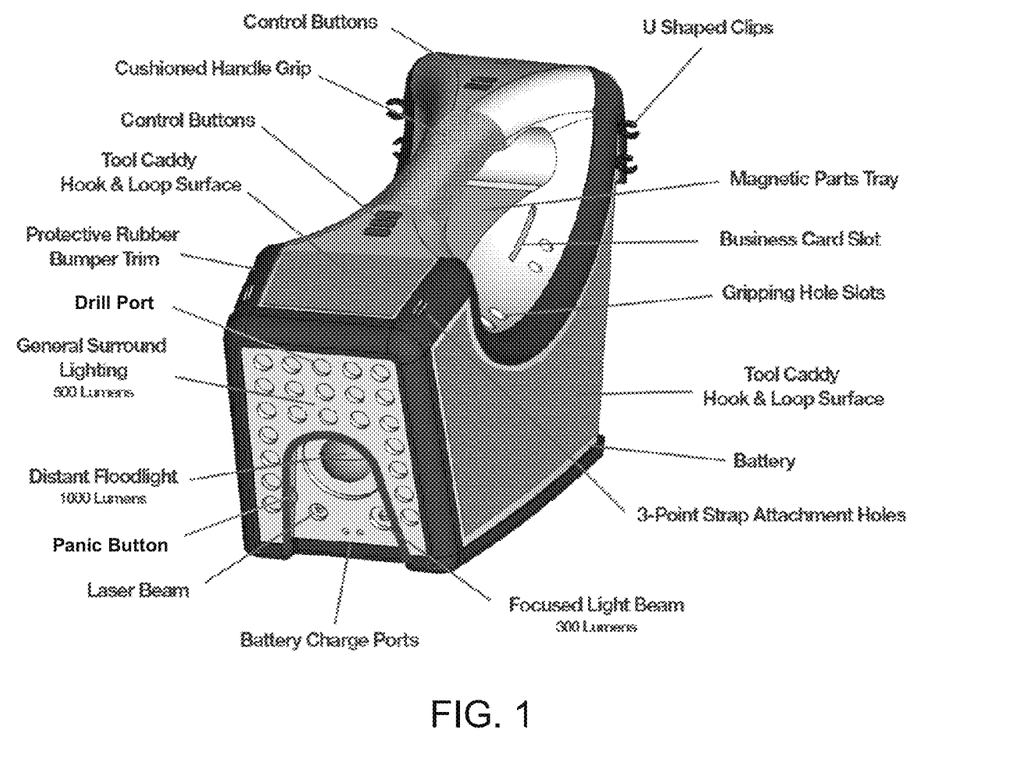
FIG. 1 is one view of an embodiment of the multitask multifunction apparatus for building inspection.
Figure 2:
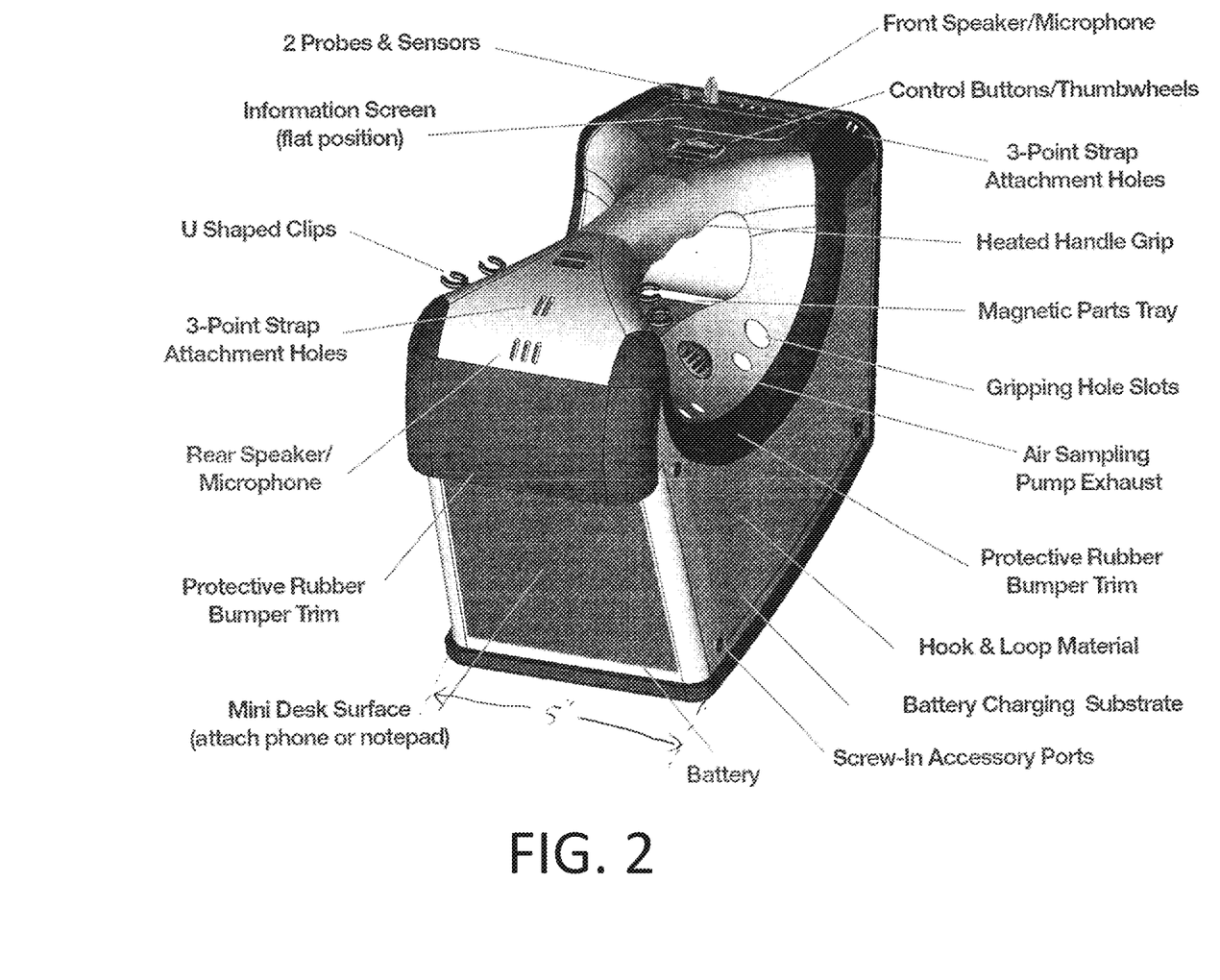
FIG. 2 is an alternate view of an embodiment of the multitask multifunction apparatus for building inspection.
Figure 3:
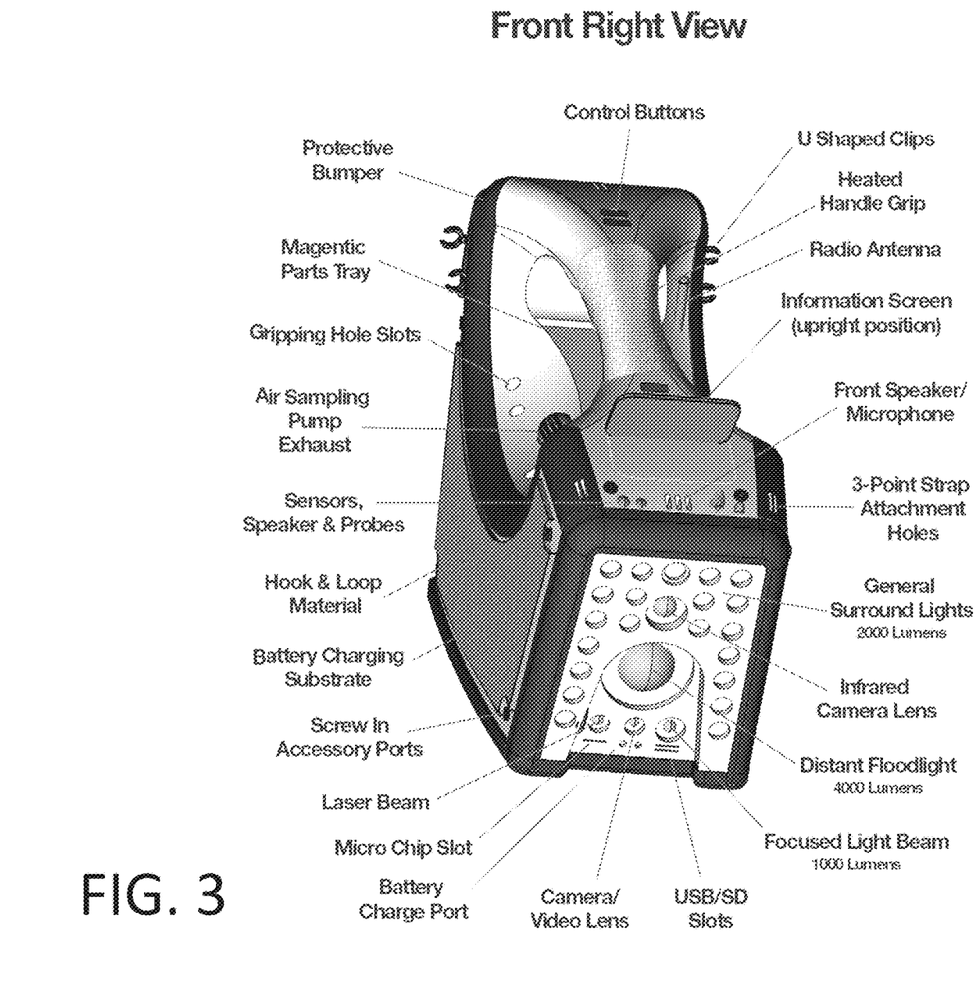
FIG. 3 is an alternate view of an embodiment of the multitask multifunction apparatus for building inspection.
Figure 4:
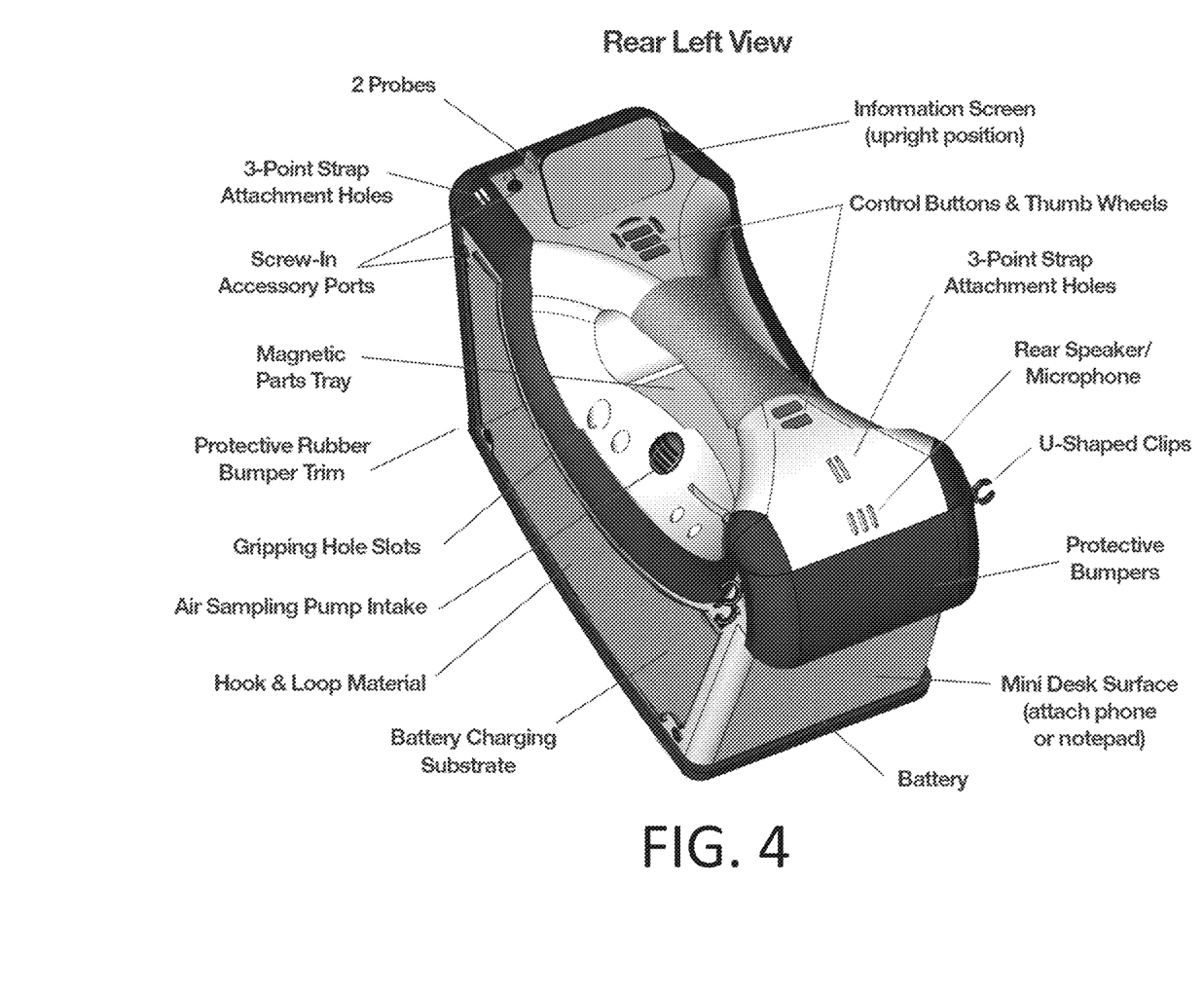
FIG. 4 is an alternate view of an embodiment of the multitask multifunction apparatus for building inspection.
Figure 5:
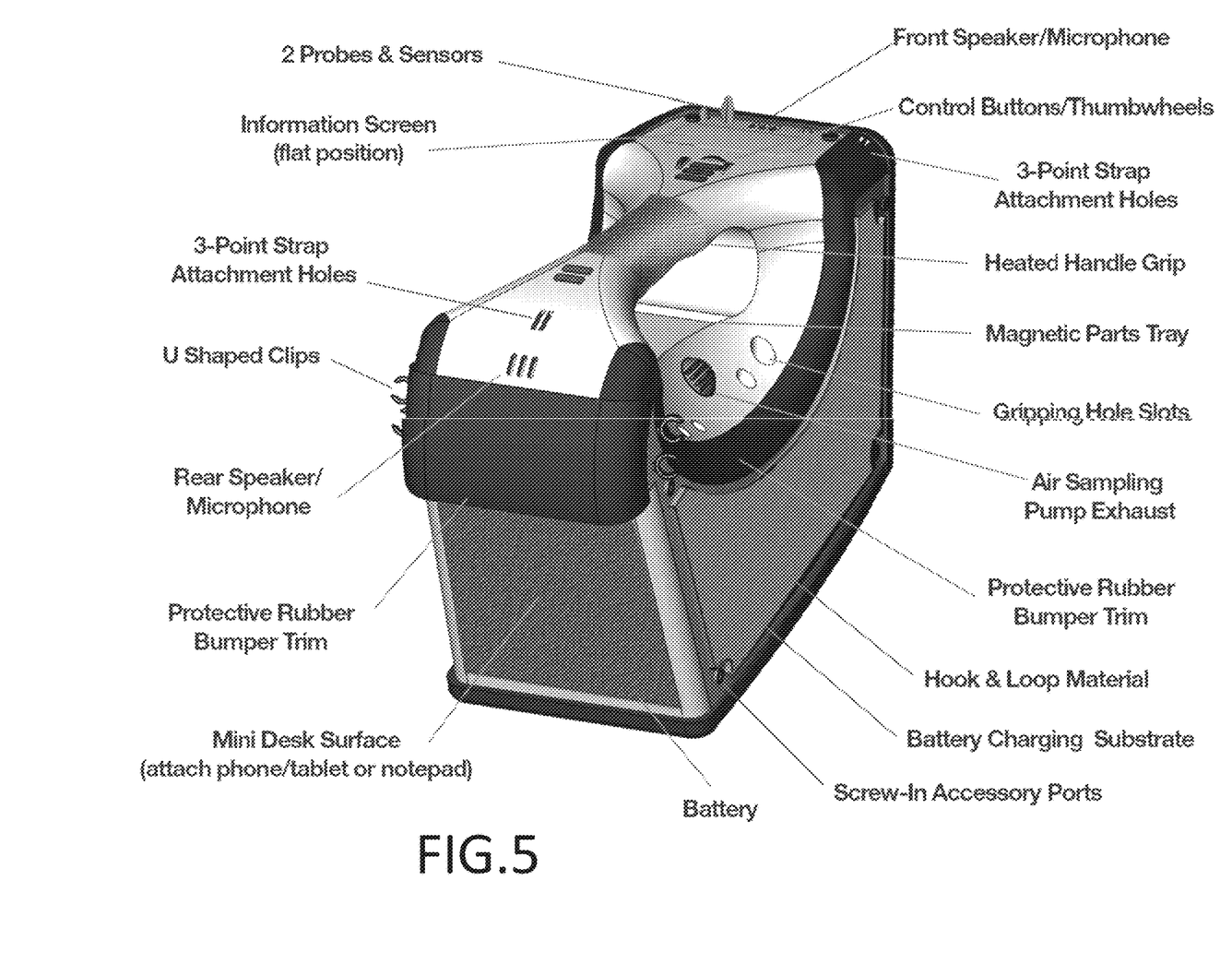
FIG. 5 is an alternate view of an embodiment of the multitask multifunction apparatus for building inspection.
Figure 6:
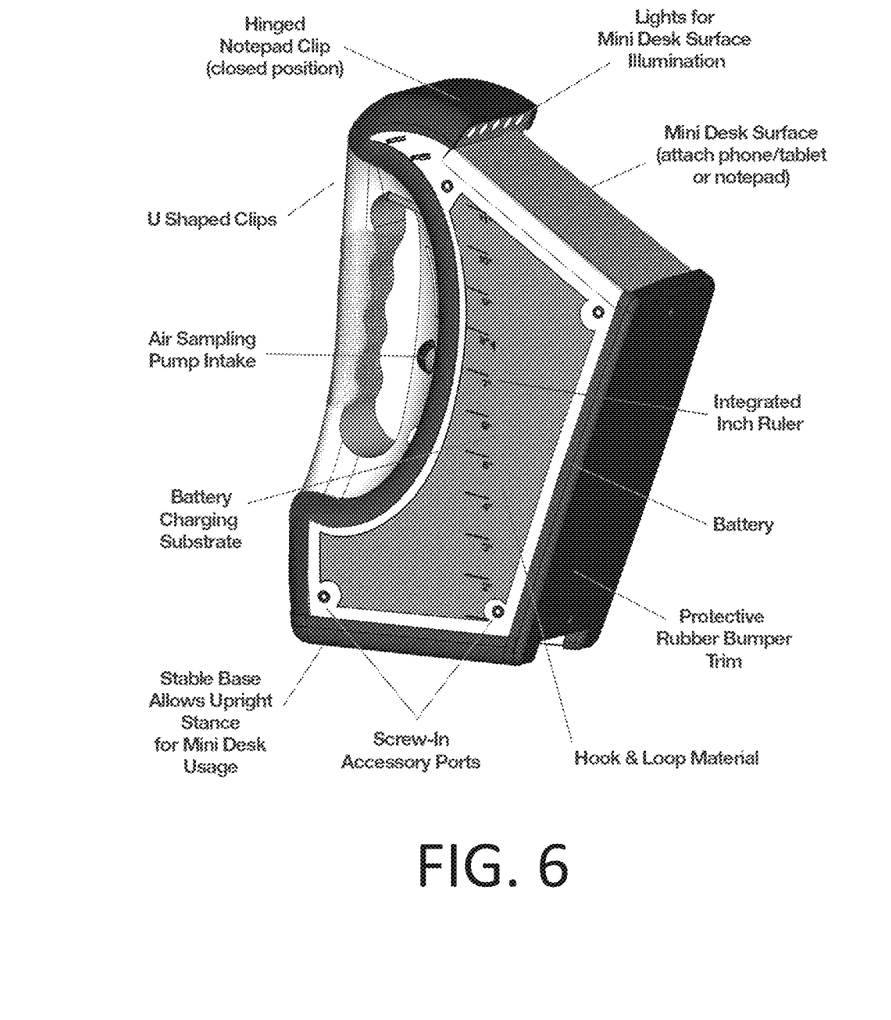
FIG. 6 is an alternate view of an embodiment of the multitask multifunction apparatus for building inspection.

A multifunction multitask apparatus for use in building inspections is disclosed. The apparatus comprises a case comprising a grippable handle, a mini-desk, lighting elements and a plurality of sensors for building structure inspection. The apparatus includes a power source in electric communication with a sensor. The apparatus may include a variety of sensors including a voltage tester, a circuit polarity sensor, and ambient air testing sensor, and ambient temperature sensor, and ambient humidity sensor, a moisture meter, a radon sensor, a carbon monoxide sensor, and an airborne toxin sensor. Other embodiments of the invention may include safety features including a first-aid cat, a chemical spray deterrent device, and a tactical prong. Other embodiments may include lights including a laser pointer, an LED light, an a focused light beam.

DETAILED DESCRIPTION

The following description of a multitask multifunction device of the invention, describes the general configuration, utility, and advantages of the invention. Those skilled in the art will appreciate that the invention can be practiced in alternative embodiments, consistent with this disclosure, and is not limited to any particular configuration or embodiment.

A multitask multifunction apparatus is disclosed. The apparatus includes multiple instruments and tools used by property inspectors and other building trades professionals during the inspection of building structures and/or surrounding areas.

During an inspection, the person performing the inspection will measure and verify any of a large number of potential building characteristics. These may include: the compaction and grading of the surround property; hazards relating to trees and other landscaping near the building; integrity of fences, railings, and other partitions; width and condition of sidewalks and pathways; structure of steps and porches; the integrity of the building foundation; integrity of windows and doors; extent of insulation and compliance with energy conservation regulations; integrity and composition of roof materials; determination of proper ventilation; determination of proper lighting; determination of adequate means of egress; condition of various building systems, including water, sewer or septic system, plumbing fixtures, drains, electrical service, wiring, and fuse/break box; and grounding of electrical system.

Embodiments of the apparatus disclosed include a combination of instruments and sensors, each of which is generally recognized and used in the art individually, and provides the tools needed by a property inspector or building trades professional in one portable handheld device.

In one embodiment of the invention, the outer case of the apparatus is made of a thermoplastic elastomer. Alternatively, the outer case may be made from any suitable materials, including plastics, metals, and composites. The case is preferably waterproof and impact resistant. The outer case includes a handle with a shape suitable for firmly gripping the apparatus with one hand, allowing the inspector to use the other hand to access and maneuver through the structure. The handle may have multiple finger grips, made of a soft cushioning material below the surface. The surface may be made of a non-slip material for positive gripping. The edges of the case may be covered in a protective bumper material, such as a dense foam or resilient edging material. In some embodiments of the apparatus, various strap attachment points may be located around the device to facilitate the use of a shoulder strap, lanyards, or other means of handling the apparatus during use.

In some embodiments, apparatus may include a "Mini-Desk" surface to permit the inspector or building trade professional to write or work on a firm, flat, and clean surface. In some embodiments, the selected surfaces of the apparatus, including the sides, top-front, and Mini-Desk may include portions covered in "hook & loop" material. This allows the user to attach frequently used small instruments to the apparatus case and thus eliminate the need for a cumbersome "tool belt", "fanny pack", "pocket stuffing" or repeated trips into and out of the inspection area to retrieve items from a tool box or vehicle. The ability of the inspector to quickly and conveniently attach and detach small instruments to the hook & loop material allows the inspector to more quickly move through the required inspection tasks.

The case may also comprise a "Magnetic Tray" located at the top center surface of the cases below the handle. The shallow tray provides a space to conveniently, firmly hold and keep track of screws, nails, and other mall metallic objects.

In some embodiments, a "Wireless Battery Charging Station Substrate" may be located below the hook and loop material to continuously charge the battery for instruments adhered to the hook and loop material.

Various embodiments of the invention may include a selection of sensors and measuring devices or tools depending on the nature of the inspection or the type of building structure at issue. The selection of sensors and measuring devices may vary between embodiments based on the particular applications necessary. In some embodiments, for example, the sensors and measuring devices include a voltage tester and/or ambient air testing sensors to determine the presence of mold and other toxins. Both an air pump intake and exhaust may be located on the devices as well as various sensors depending on which chemicals or gasses need to be monitored. The apparatus also may include temperature and humidity sensors located on the top surface of the case to collect inside and outside ambient temperature and humidity.

The selection of sensors and instruments incorporated into the device may be modular to permit the selection of sensors and instruments appropriate for a particular project. For example, an inspection or evaluation involving electrical system should include sensors and instruments appropriate for assessing a building electrical system, such as polarity meters, voltage meters, and the like. Alternatively, a device suitable for inspections of basements may include moisture meters, radon sensors, carbon monoxide sensors, and the like.

In some embodiments, the case may include a integrated English 11 inch metric scale with markings along the sides that is helpful when the case is positioned in a resting position. This gives the inspector a quick check of step riser and tread dimensions for stairs and landings and isolation distances.

Some embodiments of the apparatus will include one or more safety features integrated into the case. The selection of safety features incorporated into the device may be modular to permit the selection of those appropriate for the hazards likely to be encountered in a particular structure or project. One safety feature may include a first aid kit to provide relief in case the inspector suffers an injury and other safety feature may be an EpiPen, to provide relief to an inspector if they suffer an allergic reaction to a material encountered in the confined space. An alternative safety feature is a panic button, which the inspector can trigger to provide notice that their injured or have encountered an unexpected danger. The panic button may be used to trigger any combination of sonic blasts, flashing lights, or communicate to a 911 or other emergency service.

Some embodiments of the apparatus will include one or more components used to ward off animals, insects, or other threats encountered in the inspection space. For example, the apparatus may include a chemical spray to deter attacks. In other embodiments of the apparatus may include tactical prongs located on the top and side of the case to physically ward off attacks.

The apparatus may also include a drill port allowing the insertion of a drill bit to bore small holes to access the interior of the structure such as beams and other support members.

The device may include general lighting, a focused light beam, a distant flood light, and a laser pointer on the front of the device. In addition, LED lights may be available on the back end in such a configuration as to illuminate an attachable note pad. Furthermore, the front also may contain both a regular and infrared video camera lens, a battery charging port, and USB/SD slots. An information screen as well as control buttons may be located on top of the device with multiple speakers in the front and rear.

The lighting elements may include any one or more of the following light sources:
"Distant Floodlight"—This light is at the front facing of the case, with a capacity from 1,000 up to 4,000 Lumens. This dimmable powerful broad beam provides a wide field of light for use in unlit areas, such as in attics and crawlspaces.

"Focused Beam Light"—This light is at the front facing of the case, with a capacity from 300 up to 1,000 Lumens. This dimmable beam is useful for inspecting into a confined space where a specific location needs an intense tight beam. For example, the light may be used to examine deep inside of a heat exchanger at a suspect crack, or to examine wall cavities. This light comes with an LED white & red chip. The red intense tight beam can cut through furnace flames to see cracks in the heat exchanger while the warming up metal expands the crack open.

"General Surround Light"—This light is at the front facing perimeter of the case with a capacity from 500 up to 2,000 Lumens. This provides a general surround illumination of a specific work area.

"Laser Beam"—This is at the front facing of the case, where it provides three purposes—surface temperature, length measurements and is an instructional pointer.

The power source for the sensor may be rechargeable and permit use of the instruments and sensors for a suitable period of time to complete the inspection of a property, which may take several hours. In alternative embodiments, the power source may be a replaceable battery pack or individual batteries sufficient to provide the voltage necessary to power the apparatus for the duration of an inspection. In some embodiments a portable solar panel may be attached to charge the power source.

An embodiment may use a rechargeable battery pack as a power source for all powered features of the apparatus. A 12V bus may be used to supply power to high-energy peripherals (such as the drill motor or lights) and may be generated from the battery pack using a voltage converter. In addition, a 5V bus powers the Embedded Computer and is generated from the battery pack using a voltage converter. In some embodiments, a 3.3V bus powers many internal sensors and is generated from the battery pack using a voltage converter.

Rechargeable batteries may be placed in some arrangement of parallel and series. In addition to powering the internal circuits of the device, this bus may be accessible through the connector in order to allow the device to be charged from an external adapter.

A number of data interfaces may be used both inside of the device and to connect with peripherals outside of the device. At least some of the data interfaces are exposed to the outside of the device for external connection, as described in the following description. The majority of accessories plugged in to the device will connect to it over USB with the SBC acting as a host controller. A number of internal USB hubs may be employed in order to accommodate the appropriate number of ports. Any device which is said to connect to the USB Interface is assumed to connect to the Embedded Computer through one of these hubs.

A Bluetooth module may be included to host a Personal Area Network which allows external devices to connect with the device in a wireless fashion.

A WiFi router may be embedded, capable of setting up a WiFi access point to allow devices to connect when a high-speed wireless connection is needed. For example, in the cases of a wireless body camera or when using a tablet to preview the embedded cameras.

A cellular modem may be embedded in order to allow the Embedded Computer to reliably connect to a remote computer system. For example, to send location information which would allow a user to remotely identify the location of the device.

A video interface (either serial or parallel) will allow the Embedded Computer to display information to the user via an embedded screen.

Many sensors and peripherals may be plugged in to the device to extend its function. The peripherals are powered by this connector and also communicate with the host processor by way of a round, threaded, 5-pin connector bearing the following electrical signals: +5V Bus, Electrical GND, USB D+ Signal, USB D− Signal, Battery Bus.

The device may include a number of audio functions which necessitate sending and receiving audio to/from the device user. All audio sources will publish to the "Output" signal and any audio on the "Input" signal will publish to all audio sinks. An external headset plug may cause the on-board speakers/microphone to mute.

The device may have any number of data interfaces (for example I2C, UART, or SPI, commonly referred to as serial interfaces) but suitable for communication between Integrated Circuits within one device.

An ethernet interface connects an optional WiFi router and the Embedded Computer to allow high-speed data transfer. This interface may be used to transfer data between the device and another device entirely such as a smartphone or tablet.

Each feature which requires electrical connection is listed below. First, however, are a number of important feature-agnostic items which enable many features to operate.

I. Feature-Agnostic Function Blocks

The Embedded Computer (EC hereafter) may be a single-board computer in the mindset of the Raspberry Pi which includes the processor, RAM, storage, and other interfaces on a single board. This is the brain of the device which performs the following functions: Runs various software applications which reads sensors, communicates data with an application running on a cell phone, controls each of the peripherals, monitors battery voltage, displays information on the optionally embedded screen, and stores photos and videos to internal storage and facilitates transfer to external device.

The EC may be configured to attach to the following interfaces: 5 Volt Bus, Battery Bus, USB Interface, Bluetooth Interface, WiFi Interface, Cellular Interface, Video Interface, Audio Interface, Serial Interface, and Ethernet Interface.

Because many of the devices and peripherals connect to the device via USB, a number of USB hubs may be used to connect each device and port back to the EC. These hubs may be connected to the 5V power bus and the USB Interface of the EC.

Certain, always-connected, features may be configured in the device to make an internet connection independent of any surrounding wireless network. These features may be enabled using a a cellular modem connected to the EC so that the EC can send and receive data from remote servers. The data modem is connected to the 5V power bus and the USB Interface of the EC.

A Bluetooth receiver may be included to create the Bluetooth interface and be controlled by the EC. In addition to providing data and control between the EC and outside devices, it can also allow the outside devices to use the Speakers and Microphone (A-8) of the device as a "hands-free audio device". The Bluetooth Receiver is connected to the 5V power bus and the USB Interface of the EC.

A apparatus of the invention may be configured to include an embedded WiFi router allowing the device to become a WiFi hotspot in order to allow faster wireless data transfer where necessary. The router connects to the EC via the Ethernet Interface and is powered by the 12V Bus.

II. Functional Blocks by Feature

A removable battery pack may be built of a number of batteries in parallel and in series optimized for power sourcing. The battery pack also includes a temperature sensor which is connected to a microcontroller which can convey this information to the EC. The microcontroller is connected to the 3.3V Bus and communicates with the EC via a serial interface.

A distant flood light is formed from a number of LED modules arranged to provide the appropriate light level. This circuit also includes a switching transistor and temperature sensor which are connected to a microcontroller which can communicate with the EC to receive instruction and convey sensor information to the EC. The circuit is powered by the 12V bus.

A round, threaded port is provided in some embodiments which allows for a peripheral or battery charger to be connected. The connector provides external access to the following internal signals: +5V Bus, Electrical GND, USB D+ Signal, USB D− Signal, and Battery Bus.

A battery pack charger comprises a voltage regulator, microcontroller, and USB connection to the EC. Regulated voltage and EC communication are connected via the Charging In & Out Ports. A software application running on the EC logs and displays state of charge of device batteries.

A wireless charging module utilizing the Qi standard may be employed in order to wirelessly charge a peripheral such as a cell phone. The charging module is connected to the 5V power bus and the USB Interface of the EC.

A retractable USB cable may be provided which coils itself via a spring and connects to one of the Screw-in accessory ports. Charging of the device battery is not capable through this cable.

The EC provides capability to host and execute software programs. Two anticipated applications will require additional sensors. The Level application will require an accelerometer and the Compass application will require a magnetometer. These additional sensors are connected to the 3.3V power bus and the Serial Interface of the EC.

A microphone and speakers allow the EC to play sounds for the user and for audio to be captured for videos or audio diaries. These devices are connected to the audio interface of the EC.

A round ⅛" audio port is provided which allows headphones and headsets to be attached to the audio interface of the EC.

A laser beam is provided in some embodiments which comprises a laser pointer to visually identify direction and a long-distance Infrared Thermometer. The laser pointer and thermometer may be connected to the 3.3V power bus and the Serial Interface of the EC.

III. "Drill Motor Port" (A-22)

The device embeds a drill motor. This circuit also includes a switching transistor and temperature sensor which are connected to a microcontroller which can communicate with the EC to receive instruction and convey sensor information to the EC. The circuit is powered by the 12V bus.

In some embodiments, the device includes USB/SD & Micro Chip Slots. In order to allow the user to transfer data to and from the device's internal storage, the device comprises an SD card controller. This controller interfaces an SD card slot as well as at least one Type A standard USB port.

The device comprises two separate cameras. Both are connected to the EC via the USB Interface and share the same architecture: a camera module connected to a microcontroller which is connected to the 5V power bus and the USB Interface of the EC.

In order to determine the pitch angle of a rooftop surface, an Accelerometer may be employed by a software application to calculate the angle between the device and the earth. The accelerometer is connected to the 3.3V power bus and the Serial Interface of the EC.

The device comprises a pressure sensor which may be mechanically fitted to a plumbing fixture in order to measure the pressure of the attached plumbing system. The pressure sensor is connected to the 3.3V power bus and the Serial Interface of the EC.

The device embeds an air pump motor. This circuit also includes a switching transistor and temperature sensor which are connected to a microcontroller which can communicate with the EC to receive instruction and convey sensor information to the EC. The circuit is powered by the 12V bus.

A screen is included which displays a Graphical User Interface generated by the EC. The screen is connected to the 5V power bus and the USB Interface of the EC.

The device comprises an internal or external probe which measures moisture. Included is a moisture sensor, connected to a microcontroller which is connected to the 5V power bus and the USB Interface of the EC.

In some embodiments, the device comprises an internal or external probe which functions as a non-contact voltage tester. Included is a transistor-based electric field sensor, connected to a microcontroller which is connected to the 5V power bus and the USB Interface of the EC.

The device comprises a "Panic" button which connects to a microcontroller and is connected to the 3.3V power bus and the Serial Interface of the EC. This button can be configurable for any purpose, but its initial intent is to help the user in an emergency situation by emitting a sound or dialing an emergency phone number on an attached device.

Some embodiments of the apparatus may include an electrical heating element which is embedded within the device handle. This circuit also includes a switching transistor and temperature sensor which are connected to a microcontroller which can communicate with the EC to receive instruction and convey sensor information to the EC. The circuit is powered by the 12V bus.

The device comprises internal or external probes which measure concentrations of specific gases. For external probes, different attachment tips are used to detect different gases. Sensor is connected to a microcontroller which is connected to the 5V power bus and the USB Interface of the EC.

The device comprises internal or external probes which measure air quality. For external probes, different attachment tips are used to detect different gases. Sensor is connected to a microcontroller which is connected to the 5V power bus and the USB Interface of the EC.

Sensors are connected to a controller which communicates over USB.

IV. " " (B-44)

The device comprises internal or external probes which measure concentrations of specific gases such as Halide and Freon. For external probes, different attachment tips are used to detect different gases. Sensor is connected to a microcontroller which is connected to the 5V power bus and the USB Interface of the EC.

Peripheral to the device is a body-worn camera capable of sending video and still images over a wife network to the device. The body camera comprises a camera module connected to a controller which relays information to the device via WiFi interface. The body camera is powered by its own batteries.

The device may include an internal or external probe which functions as an electromagnetic field sensor. Included is an emf sensor, connected to a microcontroller which is connected to the 5V power bus and the USB Interface of the EC.

With respect to the above, it is to be understood that the invention is not limited in its application to the details of construction and to the arrangement of the components listed or the steps set forth in the description or illustrated in the drawings. The various apparatus and methods of the disclosed invention are capable of other embodiments, and of being practiced and carried out in various ways that would be readily known to those skilled in the art, given the present disclosure. Further, the terms and phrases used herein are for descriptive purposes and should not be construed as in any way limiting.

As such, those skilled in the art will appreciate that the conception upon which this disclosure is based may be utilized as a basis for designing other inventions with similar properties. It is important therefore that the embodiments, objects, and claims herein, be regarded as including such equivalent construction and methodology insofar as they do not depart from the spirit and scope of the present invention.

It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

I claim:

1. A multifunction multitask apparatus for building inspection, comprising: a case having a front end, a rear end, a first side, and a second side, the front end having a recessed portion and configured to support the case in an upright position; a plurality of first lighting elements disposed at the front end of the case adjacent the recessed portion, a floodlight disposed in the recessed portion at the front end of the case; a laser beam pointer disposed adjacent to the floodlight in the recessed portion, the laser beam pointer configured to at least one of provide an instructional pointer, sense a surface temperature, and measure a length; a plurality of sensors configured for building structure inspection disposed on the case; a desk surface disposed at the rear end of the case, the desk surface oriented at an angle when the front end of the case is supporting the case in the upright position; a plurality of second lighting elements disposed at the rear end of the case adjacent the desk surface, the second lighting elements configured to illuminate the desk surface; a grippable handle disposed on the first side of the case between the front end and the rear end; and a power source disposed at the second side of the case and in electric communication with at least one of the sensors, the first lighting elements, the floodlight, the laser beam pointer, and the second lighting elements.

2. The apparatus of claim 1, wherein said power source is a rechargeable battery pack.

3. The apparatus of claim 1, wherein said plurality of sensors includes a voltage tester.

4. The apparatus of claim 1, wherein said plurality of sensors includes an ambient air testing sensor.

5. The apparatus of claim 1, wherein said plurality of sensors includes an ambient temperature sensor.

6. The apparatus of claim 1, wherein said plurality of sensors includes an ambient humidity sensor.

7. The apparatus of claim 1, wherein said plurality of sensors includes a moisture meter.

8. The apparatus of claim 1, wherein said plurality of sensors includes a radon sensor.

9. The apparatus of claim 1, wherein said plurality of sensors includes a carbon monoxide sensor.

10. The apparatus of claim 1, wherein said case includes a panic button disposed in the recessed portion at the front end of the case.

11. The apparatus of claim 1, wherein said case includes a drill port disposed on the front end of the case.

12. The apparatus of claim 1, wherein said plurality of sensors includes an airborne toxin sensor.

13. The apparatus of claim 1, wherein said case includes a focused light beam, the focused light beam disposed in the recessed portion at the front end of the case.

14. The apparatus of claim 1, wherein said case includes wireless communication router.

15. A multifunction multitask apparatus for building inspection, comprising: a case having a front end, a rear end, a first side, and a second side, the front end having a recessed portion and configured to support the case in an upright position; a plurality of first lighting elements disposed at the front end of the case adjacent the recessed portion; a floodlight disposed in the recessed portion at the front end of the case; a laser beam pointer disposed adjacent to the floodlight in the recessed portion, the laser beam pointer configured to at least one of provide an instructional pointer, sense a surface temperature, and measure a length; a desk surface disposed at the rear end of the case, the desk surface oriented at an angle when the front end of the case is supporting the case in the upright position; a plurality of second lighting elements disposed at the rear end of the case adjacent the desk surface, the second lighting elements configured to illuminate the desk surface; a grippable handle disposed on the first side of the case between the front end and the rear end; and a power source disposed at the second side of the case and in electrical communication with each of the first lighting elements, the floodlight, the laser beam pointer, and the second lighting elements.

* * * * *